(12) United States Patent
Yi et al.

(10) Patent No.: US 11,992,278 B2
(45) Date of Patent: May 28, 2024

(54) ROBOT FOR VASCULAR INTERVENTION

(71) Applicant: Perazah Inc., Ansan-si (KR)

(72) Inventors: Byung-Ju Yi, Ansan-si (KR); Jong Yun Won, Seoul (KR); Hyo Jeong Cha, Ansan-si (KR); Hwa Seob Song, Ansan-si (KR)

(73) Assignee: Perazah Inc., Ansan-si (KR)

( * ) Notice: Subject to any disclaimer, the term of this patent is extended or adjusted under 35 U.S.C. 154(b) by 443 days.

(21) Appl. No.: 17/315,427

(22) Filed: May 10, 2021

(65) Prior Publication Data

US 2022/0354595 A1 Nov. 10, 2022

(51) Int. Cl.
*A61B 34/30* (2016.01)
*A61M 25/00* (2006.01)
*A61M 25/01* (2006.01)
*A61M 25/09* (2006.01)

(52) U.S. Cl.
CPC ......... *A61B 34/30* (2016.02); *A61M 25/0105* (2013.01); *A61M 25/0147* (2013.01); *A61M 25/09* (2013.01); *A61B 2034/301* (2016.02); *A61M 2025/0042* (2013.01)

(58) Field of Classification Search
CPC .............. A61B 34/00; A61B 34/30; A61B 2034/301–303; A61B 34/37; A61B 34/70–71; A61M 25/00; A61M 25/0105; A61M 25/0147; A61M 25/09; A61M 2025/0042
See application file for complete search history.

(56) References Cited

U.S. PATENT DOCUMENTS

| 7,377,906 B2 | 5/2008 | Selkee |
| 7,758,564 B2 | 7/2010 | Long et al. |
| 8,137,336 B2 | 3/2012 | Ostrovsky et al. |
| (Continued) | | |

FOREIGN PATENT DOCUMENTS

| FR | 3037249 A1 * | 12/2016 | ............. A61B 34/30 |
| WO | WO-2020061240 A1 * | 3/2020 | ............. A61B 34/30 |
| WO | WO-2021011554 A1 * | 1/2021 | ......... A61B 1/00147 |

OTHER PUBLICATIONS

Machine Translation of FR-3037249, Patent Translate, pp. 1-17, printed on Jul. 17, 2023 (Year: 2016).*

*Primary Examiner* — Yi-Shan Yang
(74) *Attorney, Agent, or Firm* — Sughrue Mion, PLLC

(57) ABSTRACT

Provided is a robot for vascular intervention. The robot for vascular intervention comprises: a catheter driving unit for rotating and translating a catheter extending in a longitudinal direction while having the longitudinal direction as an axis; a guide wire driving unit provided at a side of the catheter driving unit, drawing a guide wire into the catheter by translating the guide wire, and rotating the guide wire coaxially with the catheter; a micro-catheter driving unit provided at a rear of the catheter driving unit and translating the micro-catheter in a path coaxial with the catheter that is different from draw-in and draw-out paths of the guide wire when the guide wire is drawn out from an inside of the catheter; and a micro-guide wire driving unit provided at a rear of the micro-catheter driving unit, and drawing a micro-guide wire into the micro-catheter by translating the micro-guide wire, and rotating the micro-guide wire coaxially with the micro-catheter.

12 Claims, 19 Drawing Sheets

(56) References Cited

U.S. PATENT DOCUMENTS

2010/0076310 A1* 3/2010 Wenderow ......... A61M 25/0113
600/434
2012/0179167 A1* 7/2012 Wenderow ............. A61B 34/30
606/130
2013/0035537 A1* 2/2013 Wallace ................. A61B 34/30
604/95.01

* cited by examiner

[Fig. 1]

[Fig. 3]
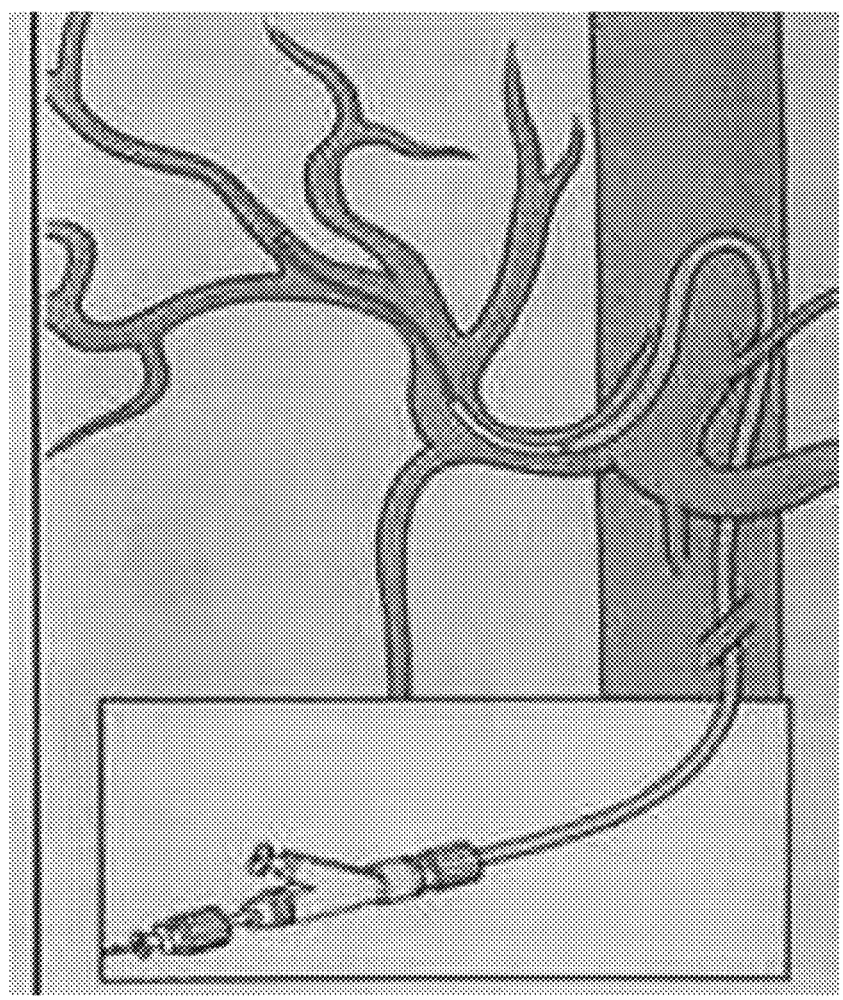

[Fig. 4]

[Fig. 5]
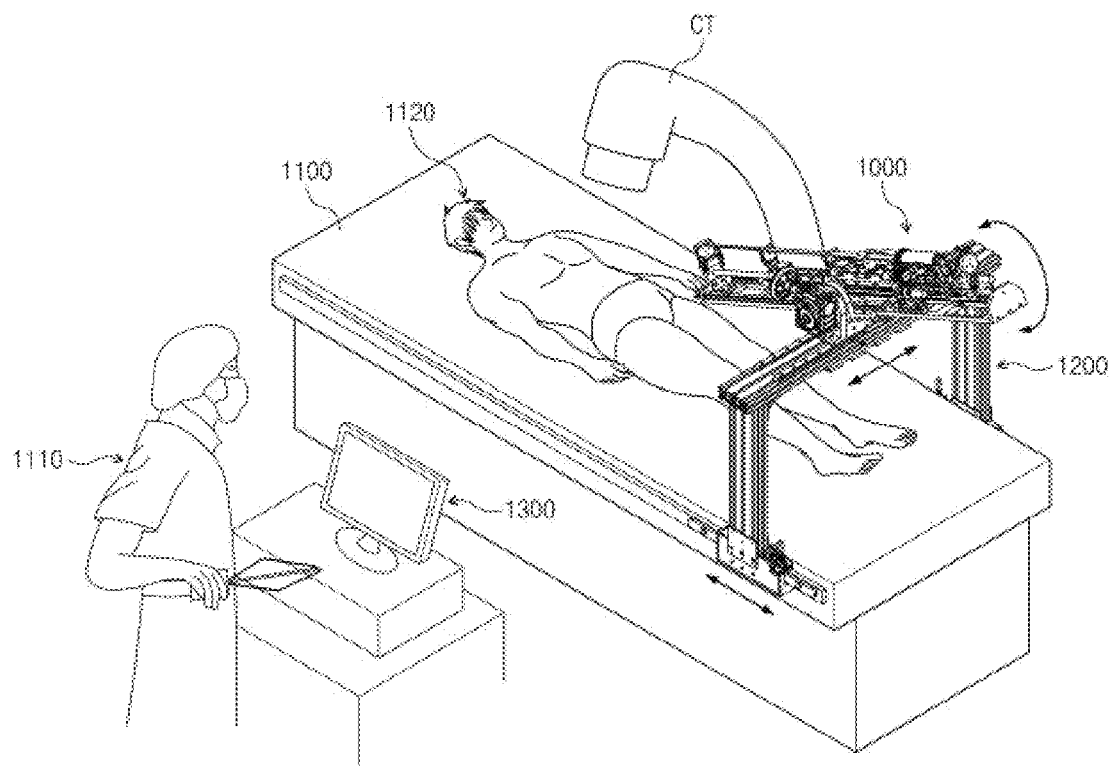

[Fig. 6]
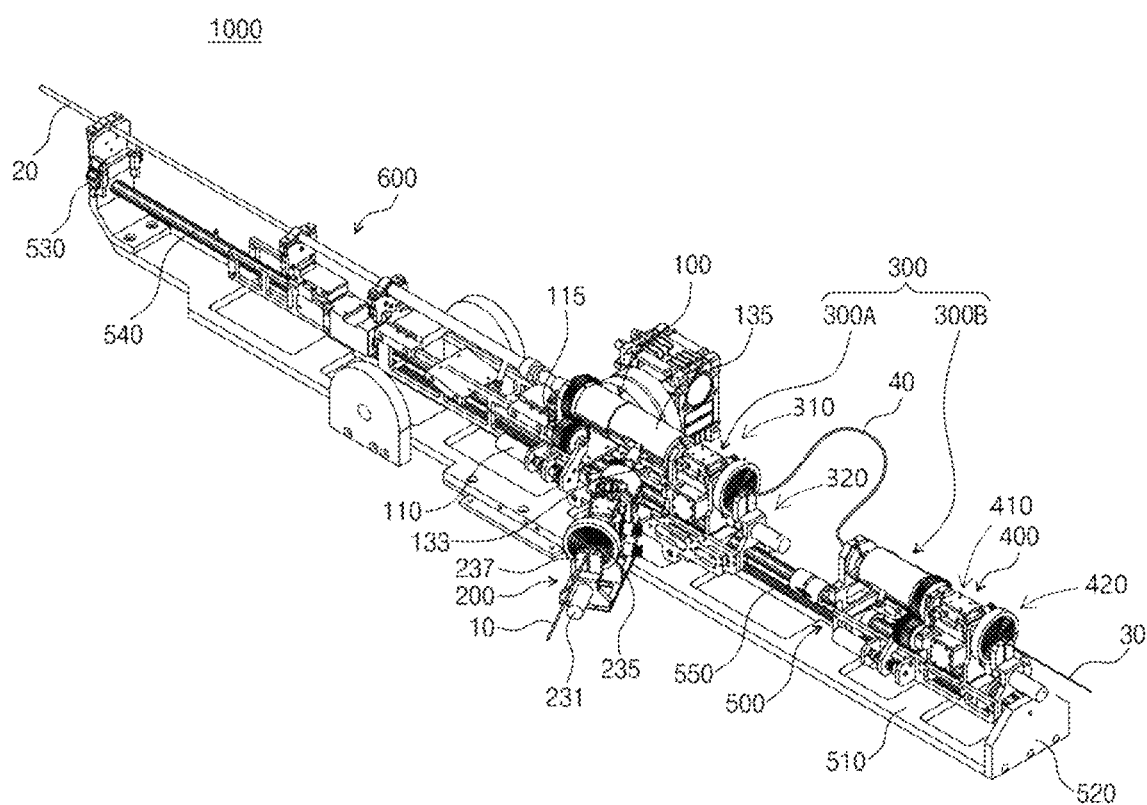

[Fig. 7]
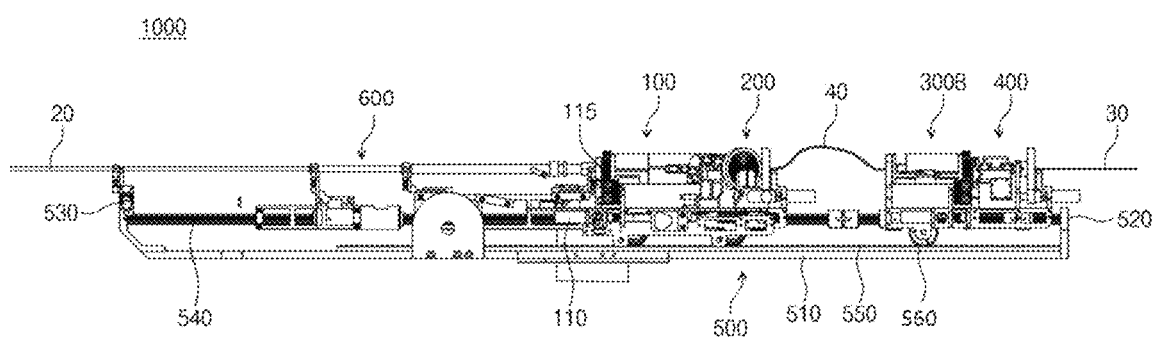

[Fig. 8]
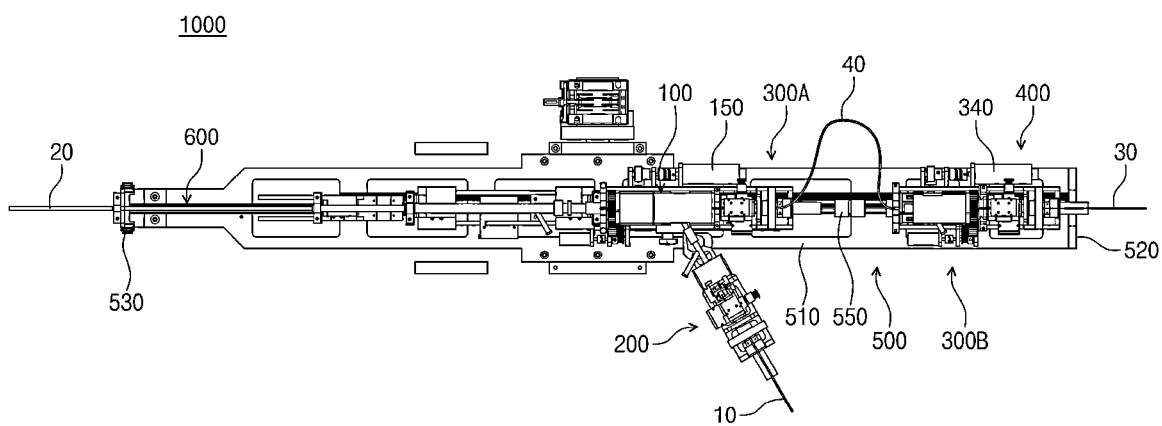

[Fig. 9]
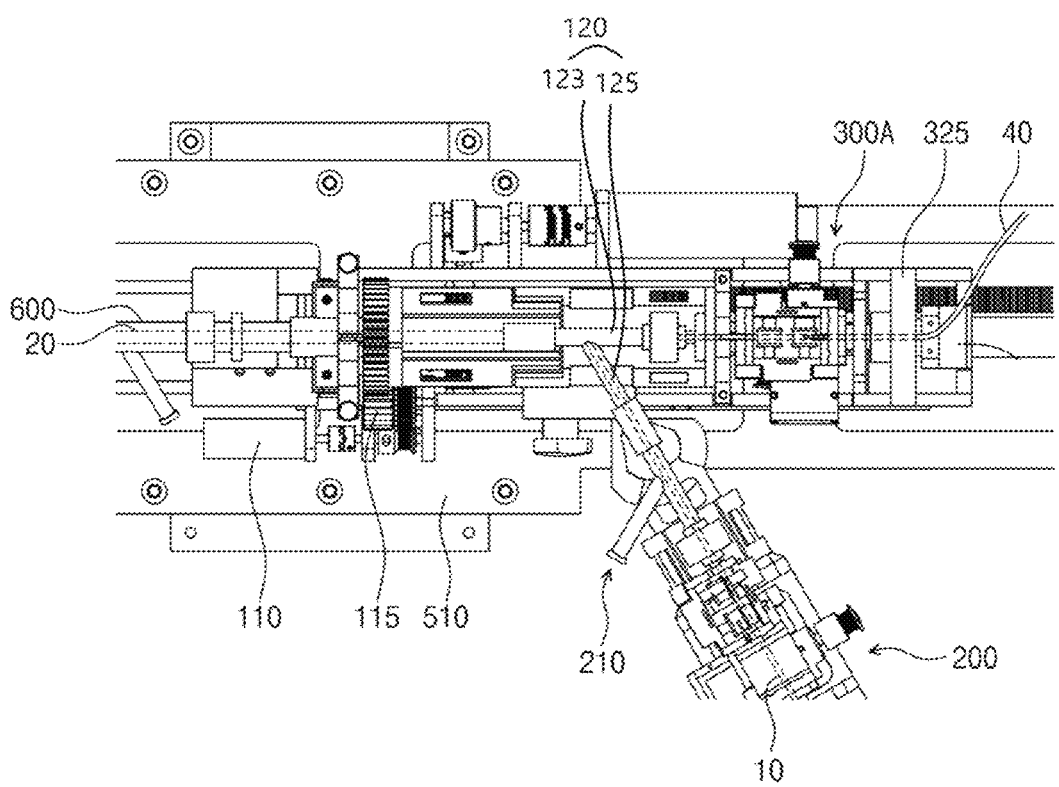

[Fig. 10]
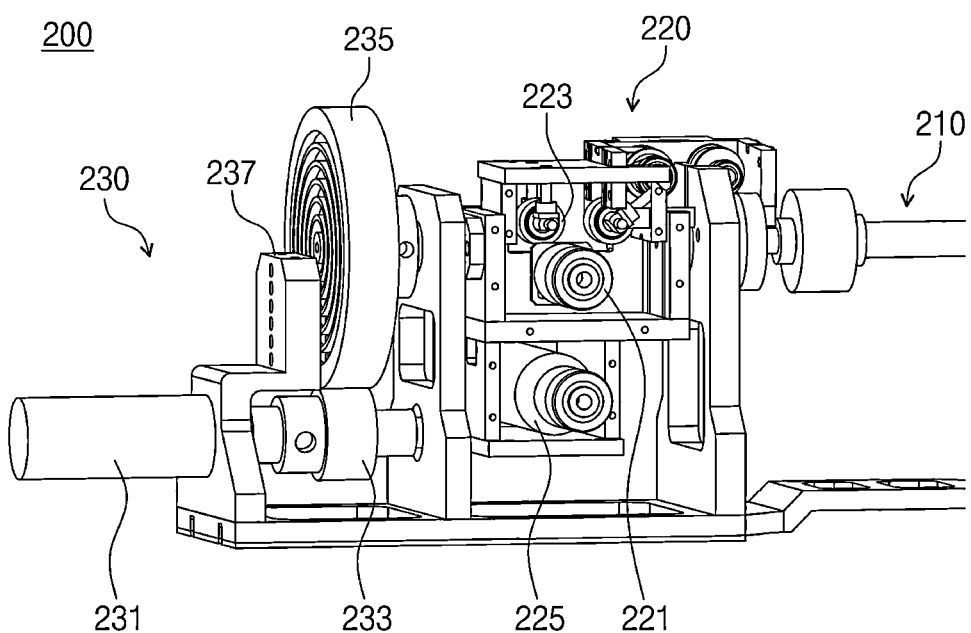

[Fig. 11]
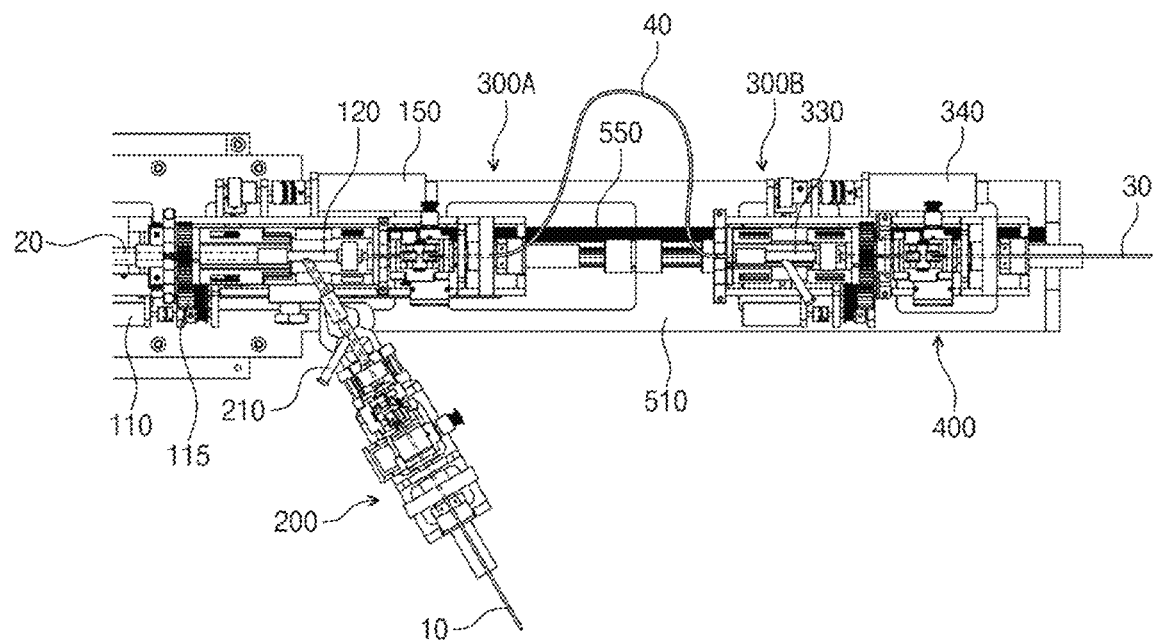

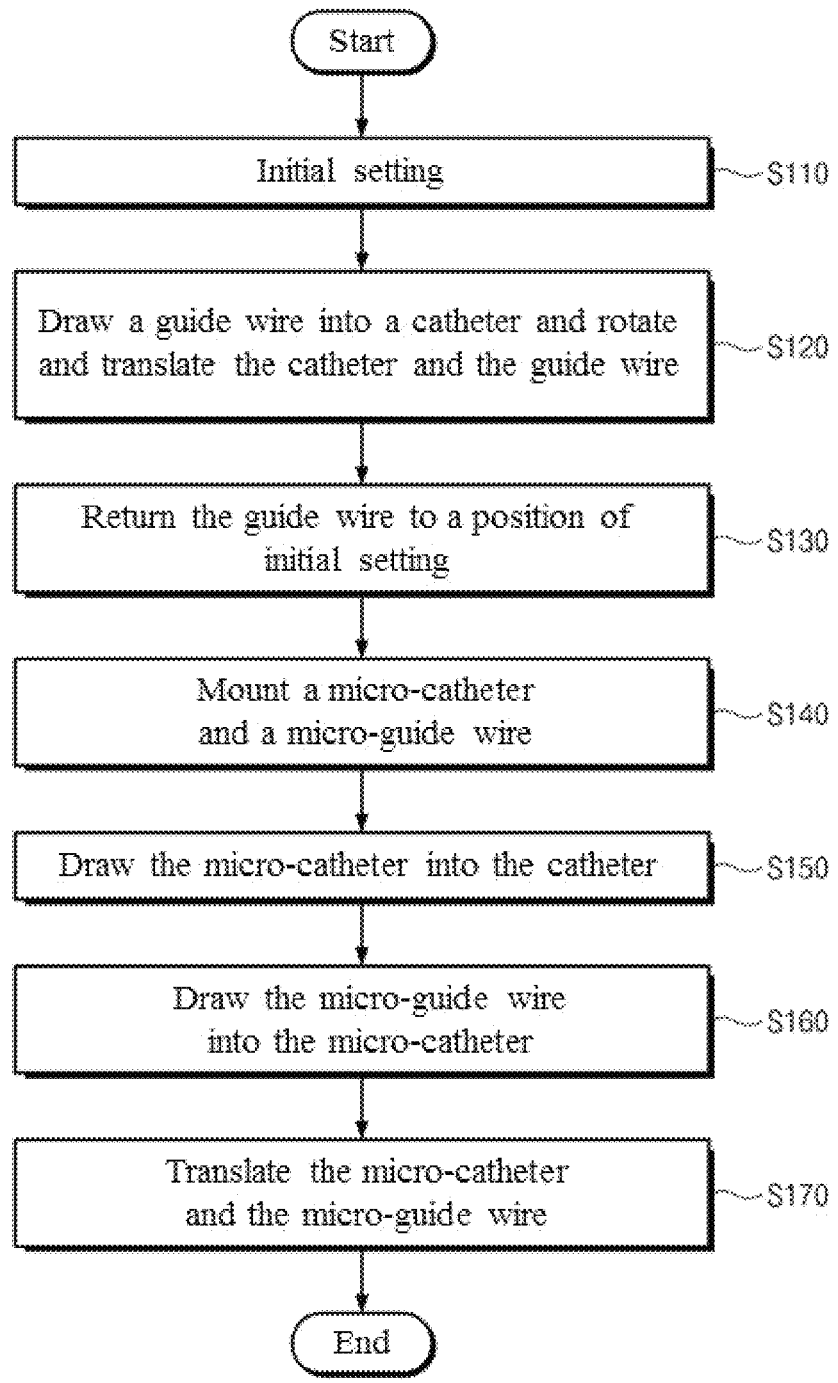
[Fig. 12]

[Fig. 13]
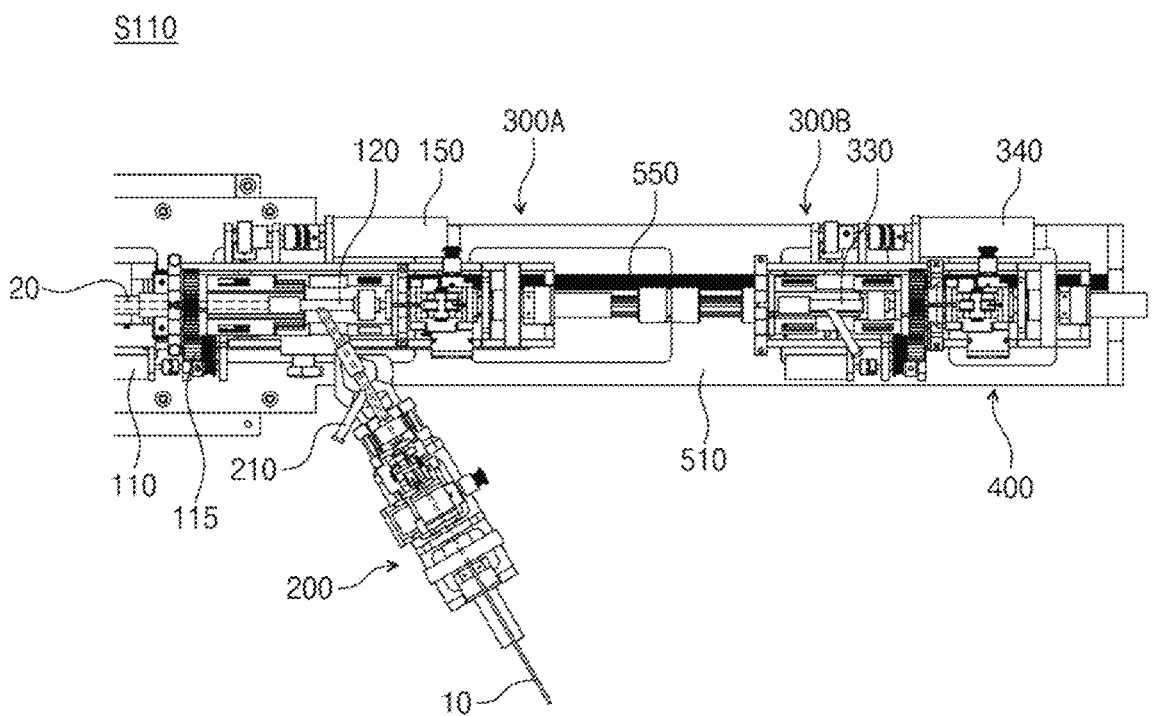

[Fig. 14]
S120
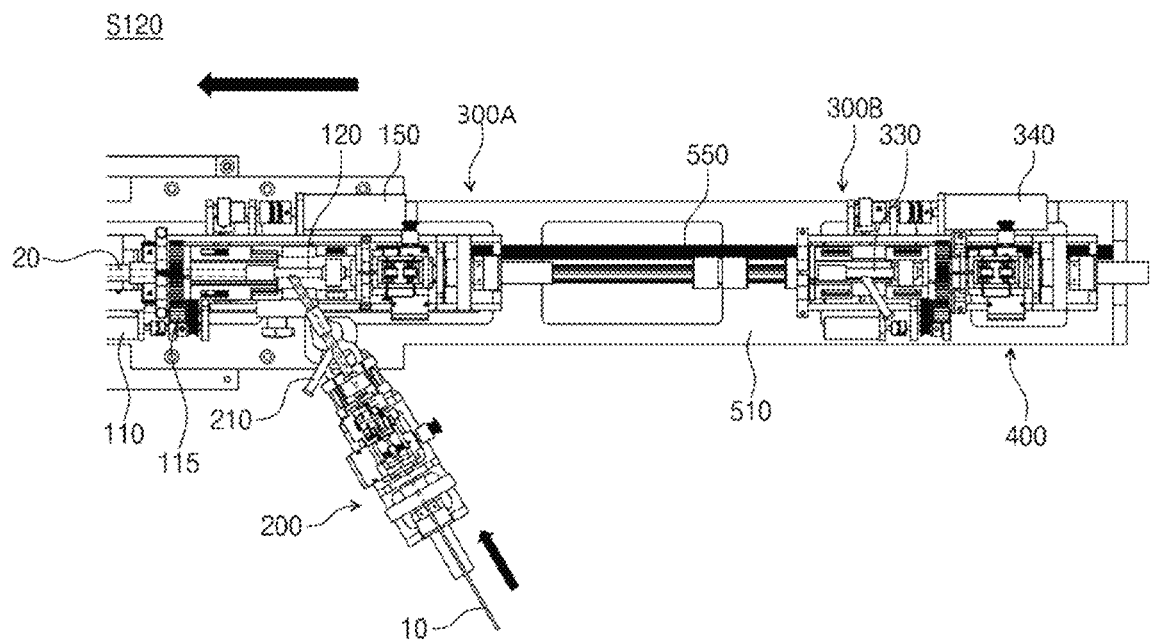

[Fig. 15]
S130
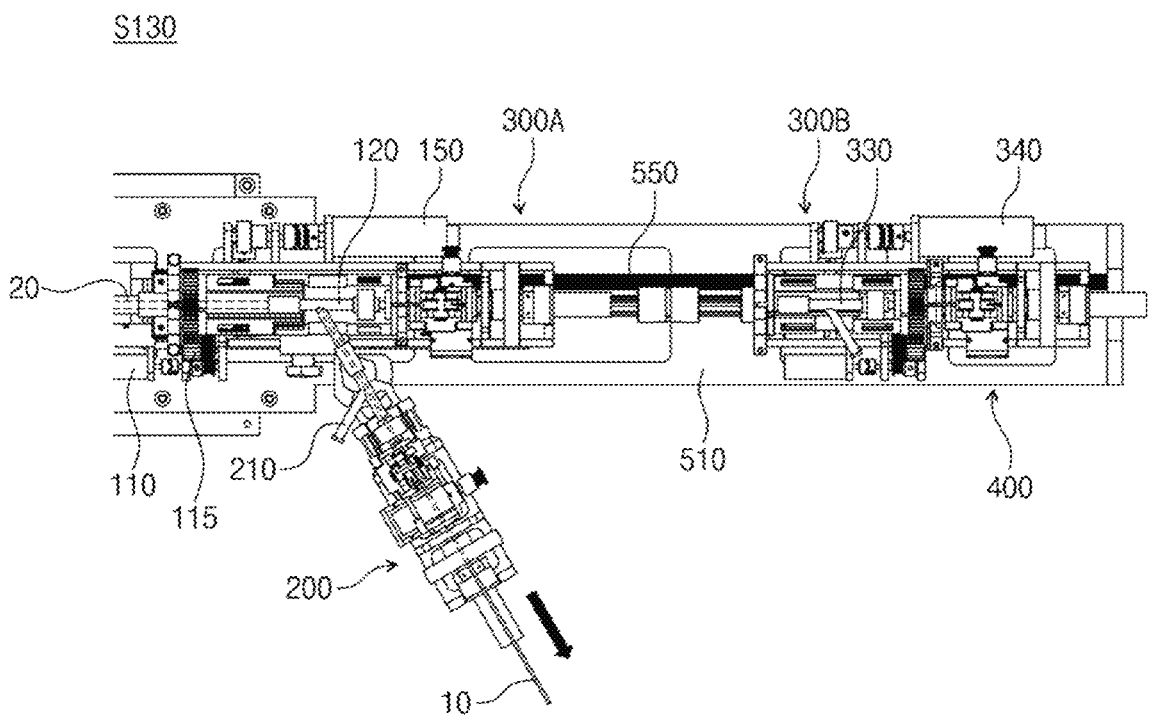

[Fig. 16]
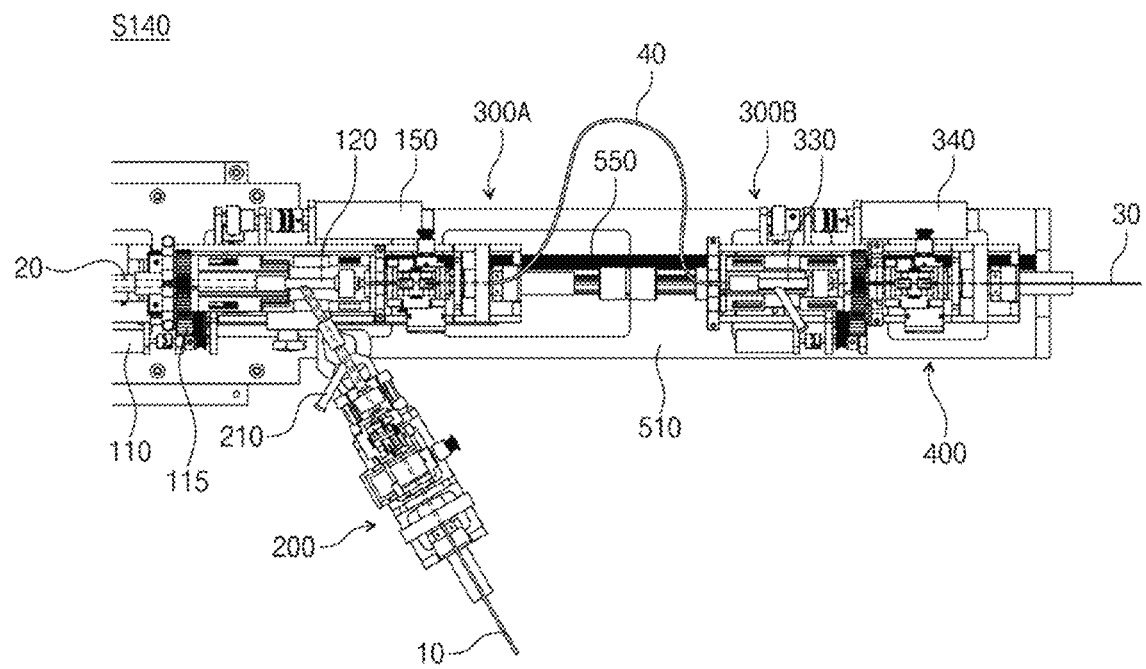

[Fig. 17]
S150
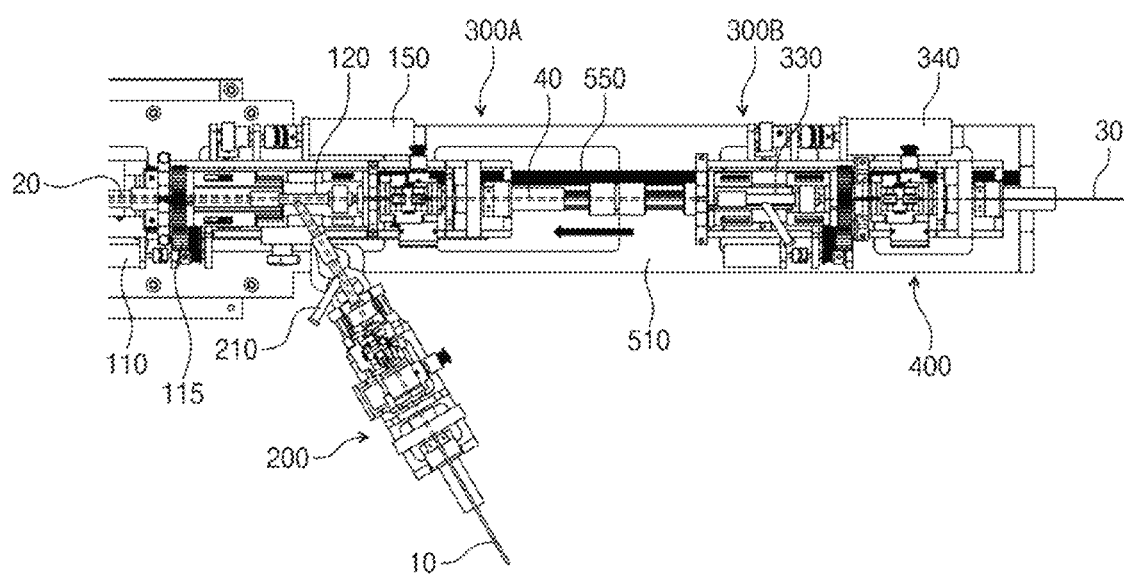

[Fig. 18]
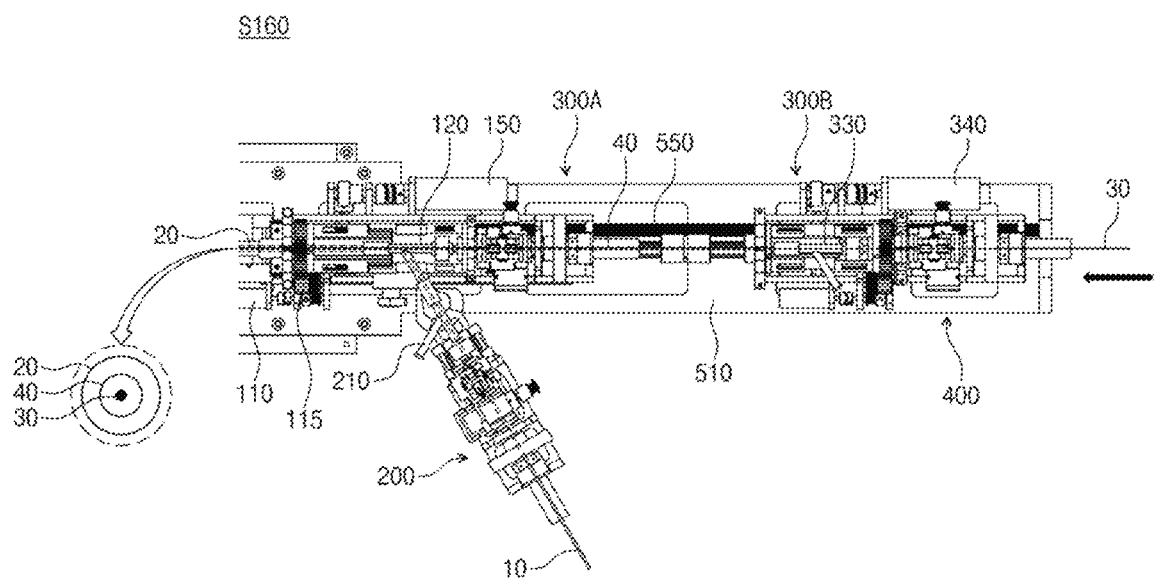

[Fig. 19]
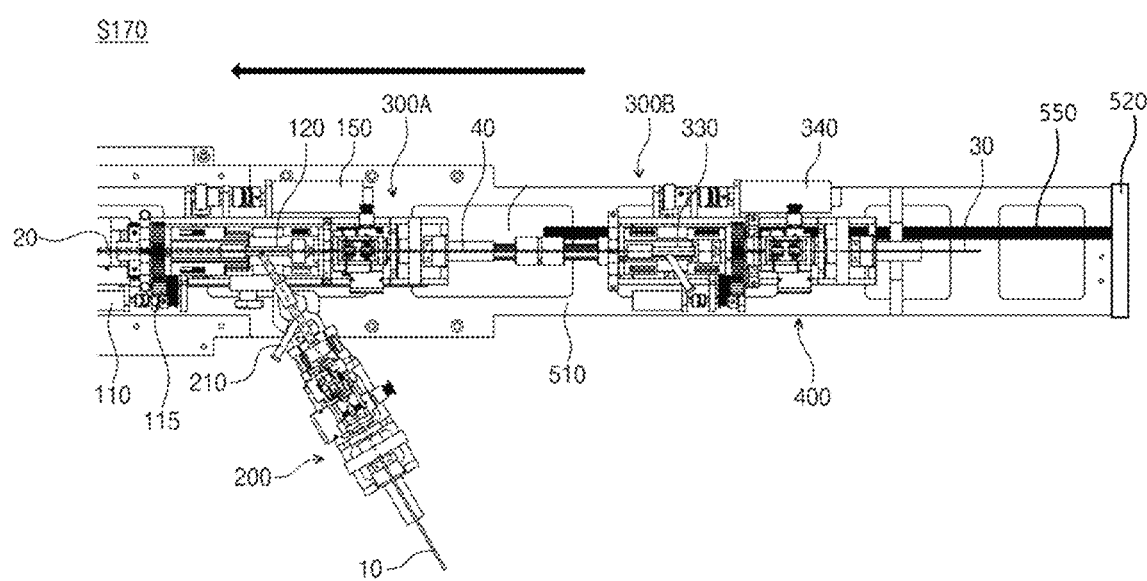

ROBOT FOR VASCULAR INTERVENTION

BACKGROUND OF THE INVENTION

1. Field of the Invention

The present invention relates to a robot for vascular intervention and, more specifically, to a robot for vascular intervention, which may improve the convenience of vascular intervention and shorten a procedure time by separating draw-in and draw-out paths of a guide wire for a catheter from draw-in and draw-out paths of a micro-catheter.

2. Description of the Prior Art

A vascular intervention is a minimally invasive procedure aimed at the treatment of vascular disease or cancer, and is performed by percutaneously inserting a thin catheter with a diameter of several mm or less up to a lesion site through a blood vessel to reach a target organ mainly under X-ray fluoroscopy. Now, representative treatments for vascular intervention performed in Korea and around the world include trans-arterial chemoembolization (TACE) for liver cancer, percutaneous angioplasty, artificial vascular stent placement for aortic disease, etc.

In particular, liver cancer is the leading cause of death, and according to data from the National Cancer Information Center published in 2011, it was shown that the incidence of liver cancer is the fifth most common in men and women after stomach cancer, thyroid cancer, colorectal cancer, and lung cancer, and the deaths from liver cancer is at the second highest level after those of lung cancer among men and women. The radical treatment of liver cancer includes a surgical resection, but most cases of advanced liver cancer that cannot be cured at the time of diagnosis undergo TACE treatment.

Specifically, TACE refers to a treatment for finding an artery that supplies nutrition to a liver tumor and administering an anticancer agent so as to block a blood vessel (see FIG. 1). A procedure is performed in an order of puncturing a femoral artery located in the groin with a needle, and accessing a guide wire, a catheter (see FIG. 2), etc. to an origin of the hepatic artery through the punctured femoral artery (see FIG. 3). Then, a hepatic angiogram is obtained while injecting a blood vessel contrast medium so as to obtain information necessary for treatment such as the location, size, blood supply pattern, etc., of the tumor, thereby determining a treatment method such as the type, dose, etc., of an appropriate anticancer agent or embolic material. When the treatment method is decided, a micro-catheter with a diameter of about 3F (1F=0.33 mm) is inserted into the origin so as to treat the tumor. The procedure time is usually about one to two hours, and may vary depending on a patient's hepatic arterial branch pattern and the complexity of a tumor arterial branch distribution.

As shown in FIG. 4, most of the blood vessels are divided into several branches or have a curved shape. Thus, the vascular intervention is performed by superimposing inserts having a diameter of several stages, called a co-axial system of a catheter and a guide wire, in order to prevent damage to the blood vessel. In addition, in the conventional vascular intervention, a master-slave system capable of remotely controlling a procedure tool has been used to reduce the radiation exposure of an operator.

However, in the conventional vascular intervention, a guide wire inserted in a catheter needs to be separated from the catheter, and then another surgical tool needs to be inserted into the catheter, in order to use surgical tools other than a guide wire, for example, a micro-catheter, a micro-guide wire, etc. Thus, in the conventional vascular intervention, since the guide wire needs to be separated from the catheter whenever the surgical tool is replaced, there is a problem of causing inconvenience for smoothly carrying out the vascular intervention, and thus delaying the procedure time, too.

SUMMARY OF THE INVENTION

One technical object of the present invention is to provide a robot for vascular intervention in which draw-in and draw-out paths of a guide wire for a catheter are separated from draw-in and draw-out paths of a micro-catheter.

Another technical object of the present invention is to provide a robot for vascular intervention capable of improving convenience of a vascular intervention and shortening a procedure time.

The technical objects of the present invention are not limited to the above.

To solve the above technical objects, the present invention may provide a robot for vascular intervention.

According to one embodiment, the robot for vascular intervention may include: a catheter driving unit for rotating and translating a catheter extending in a longitudinal direction while having the longitudinal direction as an axis; a guide wire driving unit provided at a side of the catheter driving unit, drawing a guide wire into the catheter by translating the guide wire, and rotating the guide wire coaxially with the catheter; a micro-catheter driving unit provided at a rear of the catheter driving unit and translating the micro-catheter in a path coaxial with the catheter that is different from draw-in and draw-out paths of the guide wire when the guide wire is drawn out from an inside of the catheter; and a micro-guide wire driving unit provided at a rear of the micro-catheter driving unit, and drawing a micro-guide wire into the micro-catheter by translating the micro-guide wire, and rotating the micro-guide wire coaxially with the micro-catheter.

According to one embodiment, the micro-catheter driving unit may include a front end mounting part connected to the catheter driving unit and on which a longitudinal front end of the micro-catheter is mounted; and a rear end mounting part spaced rearward of the front end mounting part, connected to the micro-guide wire driving unit, and on which a longitudinal rear end of the micro-catheter is mounted.

According to one embodiment, the catheter driving unit and the front end mounting part may be translated upon initial setting, but the longitudinal front end of the micro-catheter may not be mounted on the front end mounting part.

According to one embodiment, during a vascular intervention, the rear end mounting part and the micro-guide wire driving unit may interwork with a translational motion of the catheter driving unit and the front end mounting part, in which both longitudinal ends of the micro-catheter may be mounted on the front end mounting part and the rear end mounting part, respectively.

According to one embodiment, the catheter driving unit may include a catheter translational driving body and the rear end mounting part may include a micro-catheter translational driving body, and the catheter may translate as the catheter driving unit is moved by the catheter translational driving body, and the micro-catheter may translate as the rear end mounting part is moved by the micro-catheter translational driving body, in which, when the catheter and the micro-catheter are inserted toward a target blood vessel, the catheter translational driving body may move the catheter driving unit at a speed equal to or faster than a speed at which the micro-catheter translational driving body moves the rear end mounting part, and in which, when the catheter and the micro-catheter are drawn out from the target blood vessel, the catheter translational driving body may move the catheter driving unit at a speed equal to or slower than a speed at which the micro-catheter translational driving body moves the rear end mounting part.

According to one embodiment, upon setting for mounting the micro-catheter on the micro-catheter driving unit, the micro-catheter may have a first tension.

According to one embodiment, during a vascular intervention, the micro-catheter may have a second tension having a strength increased more than the first tension upon initial setting.

According to one embodiment, the catheter driving unit may include a first connector providing a connection passage between the catheter and the guide wire, and the catheter and the micro-catheter.

According to one embodiment, the first connector may include: a main body having a hollow formed therein, in which one longitudinal end is open to draw in and hold the catheter, and the other longitudinal end is connected to the micro-catheter driving unit; and a branch portion branched from one longitudinal side of the main body, in which a hollow is formed therein to communicate with the hollow of the main body, and a longitudinal end is connected to the guide wire driving unit.

According to one embodiment, upon initial setting, a longitudinal rear end of the catheter may be drawn into and held at one longitudinal side of the main body, and a front end of the guide wire may be disposed at a branch point side of the branch portion.

According to one embodiment, when a front end of the guide wire returns to a position of the initial setting, a front end of the micro-catheter may be disposed at the other longitudinal end of the main body.

According to one embodiment, each of the guide wire driving unit, the micro-catheter driving unit, and the micro-guide wire driving unit may include: a translational module including a plurality of conveying rollers arranged along one direction, a guide roller disposed on the conveying roller to rotate relative to the conveying roller, and a roller driving body for rotating the plurality of conveying rollers; and a rotational module connected to the translational module to rotate the translational module while having the longitudinal direction as an axis.

According to one embodiment, each of the guide wire, the micro-catheter, and the micro-guide wire may be translated by the translational module, and may be rotated by rotation of the translational module while having a longitudinal direction as an axis.

According to one embodiment, the rotational module may include: a rotational driving body; a gear coupled to a rotational shaft of the rotational driving body; and a rotational electrode plate which is rotated in engagement with the gear and includes a plurality of plated rings having a diameter gradually increasing based on an opened central axis, in which wires of the roller driving body may be individually connected to each of the plurality of plated rings.

According to one embodiment, a robot for vascular intervention may include: a catheter driving unit for rotating and translating a catheter extending in a longitudinal direction while having the longitudinal direction as an axis; a guide wire driving unit provided at a side of the catheter driving unit, drawing a guide wire into the catheter by translating the guide wire, and rotating the guide wire coaxially with the catheter; a micro-catheter driving unit provided at a rear of the catheter driving unit and translating the micro-catheter in a path coaxial with the catheter that is different from draw-in and draw-out paths of the guide wire when the guide wire is drawn out from an inside of the catheter; and a micro-guide wire driving unit provided at a rear of the micro-catheter driving unit, and drawing a micro-guide wire into the micro-catheter by translating the micro-guide wire, and rotating the micro-guide wire coaxially with the micro-catheter.

Accordingly, there may be provided a robot for vascular intervention in which draw-in and draw-out paths of a guide wire for a catheter are separated from draw-in and draw-out paths of a micro-catheter.

In addition, according to one embodiment of the present invention, there may be provided a robot for vascular intervention capable of improving convenience of a vascular intervention and shortening a procedure time.

BRIEF DESCRIPTION OF THE DRAWINGS

FIG. 3 is a schematic view showing a procedure that is performed in a state in which an insertion catheter having a diameter of 6-7F is provided at an outside and a rotatable guide wire having a diameter of 3-4F is drawn into the insertion catheter.

FIG. 4 is picture showing an example of hepatic artery chemoembolization.

FIG. 5 is a view for explaining a vascular intervention system using a vascular intervention robot according to one embodiment of the present invention.

FIG. 6 is a perspective view showing a robot for vascular intervention according to one embodiment of the present invention.

FIG. 7 is a side view showing a robot for vascular intervention according to one embodiment of the present invention.

FIG. 8 is a plan view showing a robot for vascular intervention according to one embodiment of the present invention.

FIG. 9 is a view showing a layout of a catheter, a guide wire, and a micro-catheter when a front end of the guide wire returns to a position of initial setting in a robot for vascular intervention according to one embodiment of the present invention.

FIG. 10 is a view showing a guide wire driving unit in a robot for vascular intervention according to one embodiment of the present invention.

FIG. 11 is a view showing a state in which a micro-catheter and a micro-guide wire are mounted upon setting for mounting the micro-catheter in a robot for vascular intervention according to one embodiment of the present invention.

FIG. 12 is a flowchart sequentially showing a method for driving a robot for vascular intervention according to one embodiment of the present invention.

FIG. 13 is a view showing a robot for vascular intervention in S110 of a driving method in FIG. 12.

FIG. 14 is a view showing a robot for vascular intervention in S120 of a driving method in FIG. 12.

FIG. 15 is a view showing a robot for vascular intervention in S130 of a driving method in FIG. 12.

FIG. 16 is a view showing a robot for vascular intervention in S140 of a driving method in FIG. 12.

FIG. 17 is a view showing a robot for vascular intervention in S150 of a driving method in FIG. 12.

FIG. 18 is a view showing a robot for vascular intervention in S160 of a driving method in FIG. 12.

FIG. 19 is a view showing a robot for vascular intervention in S170 of a driving method in FIG. 12.

DETAILED DESCRIPTION OF THE EXEMPLARY EMBODIMENTS

Figure 1:
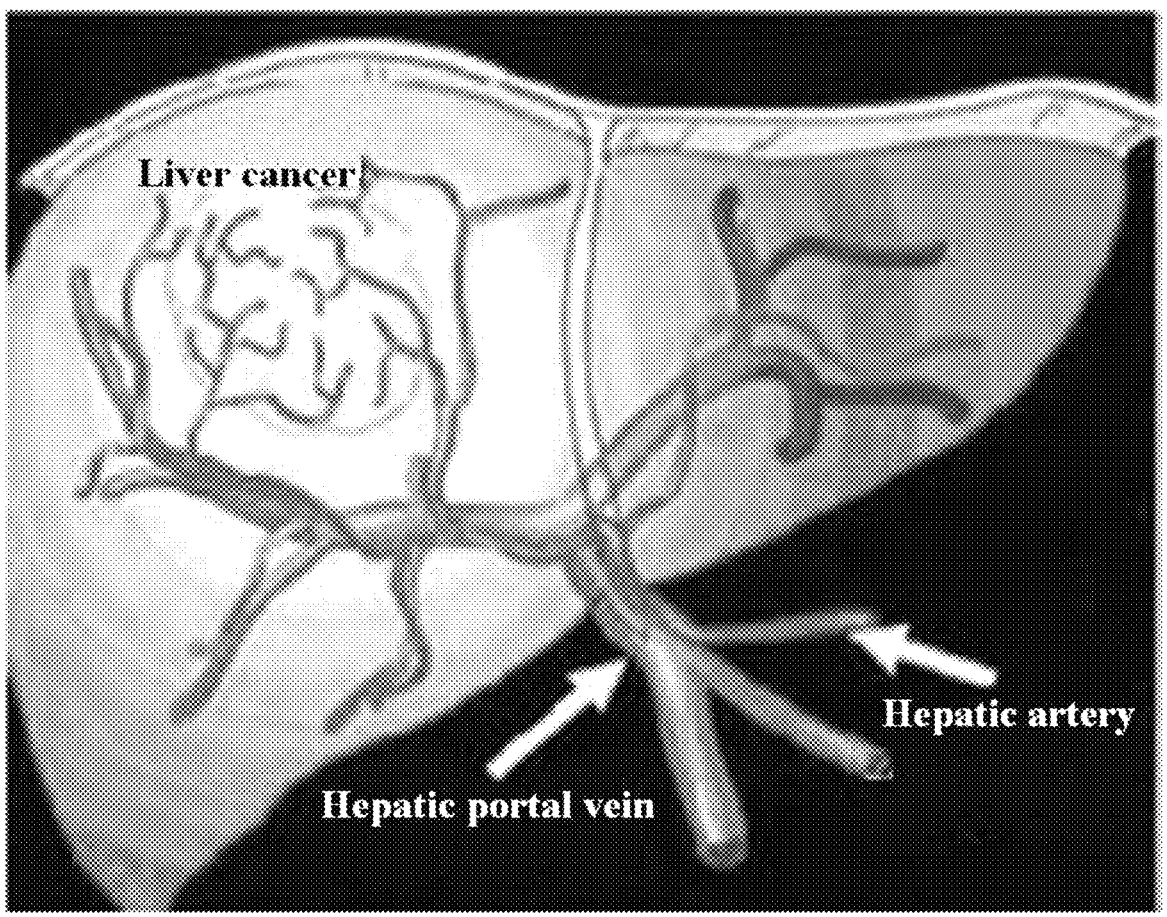
FIG. 1 is a schematic view showing liver cancer and nourishing liver arteries.
Figure 2:
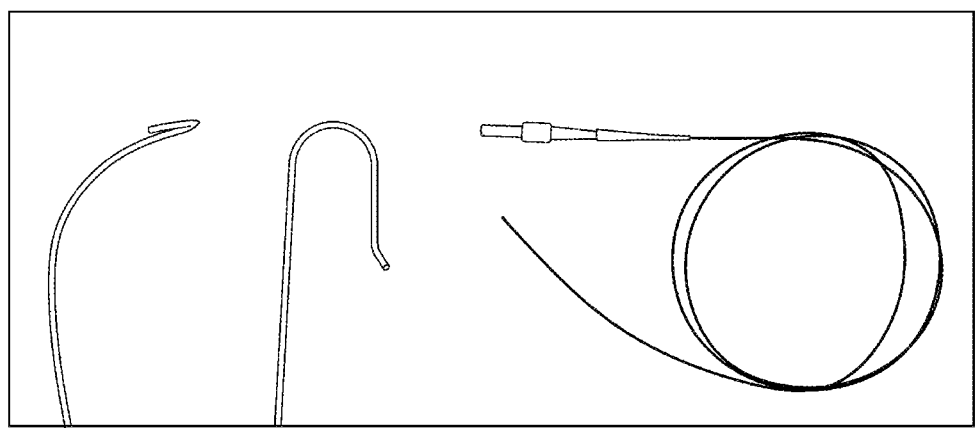
FIG. 2 is a picture showing a catheter (left) and an assembly of micro-catheter and guide wire (right) used in a TACE procedure.

Hereinafter, preferred embodiments of the present invention will be described in detail with reference to the accompanying drawings. However, the technical spirit of the present invention is not limited to the embodiments, but may be realized in different forms. The embodiments introduced herein are provided to sufficiently deliver the spirit of the present invention to those skilled in the art so that the disclosed contents may become thorough and complete.

When it is mentioned in the specification that one element is on another element, it means that the first element may be directly formed on the second element or a third element may be interposed between the first element and the second element. Further, in the drawings, a shape and a size are exaggerated for efficient description of the technical contents.

In addition, in the various embodiments of the present specification, the terms such as first, second, and third are used to describe various elements, but the elements are not limited to the terms. The terms are used only to distinguish one element from another element. Accordingly, an element mentioned as a first element in one embodiment may be mentioned as a second element in another embodiment. The embodiments illustrated here include their complementary embodiments. Further, the term "and/or" in the specification is used to include at least one of the elements enumerated in the specification.

In the specification, the terms of a singular form may include plural forms unless otherwise specified. Further, the terms "including" and "having" are used to designate that the features, the numbers, the steps, the elements, or combinations thereof described in the specification are present, and are not to be understood as excluding the possibility that one or more other features, numbers, steps, elements, or combinations thereof may be present or added. In addition, the term "connection" used herein may include the meaning of indirectly connecting a plurality of components, and directly connecting a plurality of components.

Further, in the following description of the present invention, a detailed description of known functions or configurations incorporated herein will be omitted when it may make the subject matter of the present invention unnecessarily unclear.

FIGS. 5 to 11 are views for explaining a robot for vascular intervention according to one embodiment of the present invention.

As shown in FIG. 5, a robot for vascular intervention 1000 according to one embodiment of the present invention may be applied to a vascular intervention system including a remote procedure system based on a master-slave apparatus. Here, in the vascular intervention system, an operator may remotely control a procedure from a master apparatus, and then a slave apparatus may perform the procedure on a patient according to the remote control. Accordingly, an environment in which the operator is exposed to radiation may be minimized.

First, briefly describing the vascular intervention system, the vascular intervention system may further include a bed 1100, a frame 1200, and a master apparatus 1300 in addition to the robot for vascular intervention 1000 according to one embodiment of the present invention.

The bed 1100 may provide a procedure surface on which a patient 1120 can lie down to undergo a procedure while lying down. In this case, the frame 1200 may be attached to the bed 1100 so as to be movable. One side of the frame 1200 may accommodate and fix the robot for vascular intervention 1000. For example, the robot for vascular intervention 1000 may be mounted on an upper side of the frame 1200. In this case, the robot for vascular intervention 1000 may be mounted to rotate or translate relative to the frame 1200. The other side of the frame 1200 may be attached to the bed 1100 so as to be movable. For example, the other side of the frame 1200 may be attached to a rail of the bed 1100 so as to be movable. As above, the robot for vascular intervention 1000 may be provided to rotate and translate relative to the frame 1200, thereby improving convenience of the procedure.

Meanwhile, the master apparatus 1300 may provide an interface through which an operator 1110 can remotely control the robot for vascular intervention 1000. As such, the operator 1110 may remotely control the robot for vascular intervention 1000, thereby minimizing a radiation exposure of the operator.

As shown in FIGS. 6 to 9, the robot for vascular intervention 1000 according to one embodiment of the present invention, which is applied to the above vascular intervention system, may include a catheter driving unit 100, a guide wire driving unit 200, a micro-catheter driving unit 300, and a micro-guide wire driving unit 400. In addition, the robot for vascular intervention 1000 according to one embodiment of the present invention may further include a conveying unit 500 and a catheter guide unit 600.

The catheter driving unit 100 may rotate and translate a catheter 20 extending in a longitudinal direction while having the longitudinal direction as an axis. Accordingly, the catheter driving unit 100 may insert the catheter 20 up to a target blood vessel. The catheter driving unit 100 may rotate the catheter 20 while holding the catheter 20. For example, the catheter driving unit 100 can rotate the catheter 20 while having a longitudinal direction of the catheter 20 as an axis in order to change a direction of a front end of the catheter, when the catheter 20 encounters a curved site of a blood vessel. For this purpose, the catheter driving unit 100 may include a catheter rotational driving unit 110 and a gear 115.

The catheter rotational driving body 110 may be a device that provides power to rotate the catheter 20 and may be provided as, for example, a motor. The gear 115 may receive power from the catheter rotational driving body 110 and may provide a rotational force to rotate the catheter 20. In this case, the gear 115 may be provided with a slit through which the catheter 20 can be drawn in an axial direction of the gear 115.

As shown in FIG. 9, the catheter driving unit 100 may further include a first connector 120. For example, the first connector 120 may be provided as a Y-type connector. The first connector 120 may provide a connection passage between the catheter 20 and a guide wire 10, and the catheter 20 and a micro-catheter 40. For this purpose, the first connector 120 may include a main body 123 and a branch portion 125.

The main body 123 may have a tubular shape having a hollow therein. One longitudinal end of the main body 123 may be open so that the catheter 20 can be drawn in and held. In addition, the other longitudinal end of the main body 123 may be connected to the micro-catheter driving unit 300, and thus a longitudinal front end of the micro-catheter 40 may be located at the other longitudinal end of the main body 123. However, upon initial setting for inserting the catheter 20 and the guide wire 10 into the target blood vessel, the micro-catheter 40 may not be mounted on the micro-catheter driving unit 300, and thus the longitudinal front end of the micro-catheter 40 may not be located at the other longitudinal end of the main body 123.

Like the main body 123, the branch portion 125 may have a tubular shape having a hollow therein. The branch portion 125 may be formed to branch from one longitudinal side of the main body 123. In this case, the hollow of the branch portion 125 may communicate with the hollow of the main body 123.

In one embodiment of the present invention, the guide wire driving unit 200 for rotating and translating the guide wire 10 may be connected to a longitudinal end of the branch portion 125.

Upon initial setting for inserting the catheter 20 and the guide wire 10 into the target blood vessel, a longitudinal rear end of the catheter 20 may be drawn into and held at one longitudinal end of the main body 123, and a front end of the guide wire 10 may be disposed at a branch point side of the branch portion 125. After that, when the robot for vascular intervention 1000 is operated to insert the guide wire 10 and the catheter 20 up to the target blood vessel, the guide wire 10 may move rearward and a front end of the guide wire may return to a position of initial setting. As such, when the front end of the guide wire 10 returns to the position of initial setting, the micro-catheter 40 may be mounted on the micro-catheter driving unit 300. Accordingly, the front end of the micro-catheter 40 may be located at the other longitudinal end of the main body 123.

Thus, when the micro-catheter 40 is drawn into the catheter 20, the micro-catheter 40 may be drawn in and drawn out coaxially with the catheter 20 unlike the draw-in and draw-out paths of the guide wire 10. Accordingly, when the micro-catheter 40 is drawn into the catheter 20, this draw-in may not be affected by the draw-in and draw-out of the guide wire 10, thereby improving the convenience of a vascular intervention and shortening a procedure time.

The first connector 120 may be seated in a case 133. A cover 135 may be coupled to an upper side of the case 133. The cover 135 may be coupled to the case 133 while covering the first connector 120. The case 133 and the cover 135 may serve to protect the first connector 120 from an external environment.

Meanwhile, the catheter driving unit 100 may translate the catheter 20 so that the catheter 20 can be inserted up to the target blood vessel. For this purpose, the catheter driving unit 100 may further include a catheter translational driving unit 150. The catheter translational driving body 150 may provide a driving force to a rack 550 and a pinion 560 provided in the conveying unit 500, so as to move the catheter driving unit 100 mounted on an assembly of the rack 550 and the pinion 560. The catheter 20 may translate through the movement of the catheter driving unit 100.

The guide wire driving unit 200 may be provided at a side of the catheter driving unit 100. The guide wire driving unit 200 may draw the guide wire 10 into the catheter 20 and insert the guide wire up to the target blood vessel by translating the guide wire 10, and rotate the guide wire 10 coaxially with the catheter 20.

The guide wire driving unit 200 may be connected to the branch portion 125 of the first connector 120. For this purpose, the guide wire driving unit 200 may be provided with a second connector 210 that is coupled to the branch portion 125 of the first connector 120 as a connecting device.

The second connector 210 may have the same structure as the first connector 120. Accordingly, the guide wire driving unit 200 may provide the guide wire 10 into the catheter 20 which is drawn into and held at one longitudinal end of the main body 123 through the second connector 210 and the branch portion 125 of the first connector 120.

As shown in FIG. 10, the guide wire driving unit 200 according to one embodiment of the present invention may include a translational module 220 and a rotational module 230.

The translational module 220 may be formed to include a conveying roller 221, a guide roller 223, and a roller driving body 225. Here, a plurality of the conveying rollers 221 may be provided. The plurality of conveying rollers 221 may be arranged along a direction of conveying. The guide wire 10, which is drawn in from a side of the rotational module 230 disposed rearward, may be conveyed while making a roll-contact with the conveying roller 221 and may be drawn into a side of the second connector 210 connected forward.

A plurality of guide rollers 223 may be provided. The plurality of guide rollers 223 may be disposed on the plurality of conveying rollers 221. In this case, the plurality of guide rollers 223 may be disposed to correspond to the plurality of conveying rollers 221, respectively, so as to rotate relative to each other. The guide wire 10 may pass through between the conveying roller 221 and the guide roller 223 installed as described above while making a roll-contact with the conveying roller and the guide roller.

The roller driving body 225 may be connected to the conveying roller 221 so as to provide a rotational force to the conveying roller 221. In this case, gears (not shown) may be disposed between the roller driving body 225 and the conveying roller 221, so as to transmit the rotational force generated from the roller driving body 225 to at least one conveying roller 221.

The rotational module 230 may be connected to the translational module 220. The rotational module 230 may be disposed at a rear of the translational module 220. The rotational module 230 may rotate the translational module 220 while having a longitudinal direction as an axis. Accordingly, the guide wire 10 may be translated by the translational module 220 and may be rotated while having a longitudinal direction as an axis as the translational module 220 is rotated by the rotational module 230.

For this purpose, the rotational module 230 according to one embodiment of the present invention may be formed to include a rotational driving body 231, a gear 233, a rotational electrode plate 235, and a wire guide frame 237. Here, the rotational driving body 231 may provide a rotational force to the rotational electrode plate 235. The gear 233 may transmit a rotational force generated from the rotational driving body 231 to the rotational electrode plate 235. For this purpose, the gear 233 may be axially coupled to a rotational shaft of the rotational driving body 231. In addition, the gear 233 may be gear-coupled to the rotational electrode plate 235. The rotational electrode plate 235 may be rotated in engagement with the gear 233. The rotational electrode plate 235 may be axially coupled to the translational module 220. Accordingly, when the rotational electrode plate 235 is rotated, the translational module 220 may be also rotated. In this case, a plurality of electric wires connected to an external power source may be electrically coupled to the roller driving body 225 provided in the translational module 220 so as to drive the roller driving body 225. In this state, when the roller driving body 225 is rotated by the rotation of the translational module 220, the wires may be twisted, and if this twisting phenomenon continues, some or all of the wires may be separated from the roller driving body 225 or the external power source, thereby causing an emergency situation in which the robot for vascular intervention 1000 needs to be stopped from running during a procedure. In order to solve the above problem, the rotational electrode plate 235 according to one embodiment of the present invention may include a plurality of plated rings. The plurality of plated rings may be provided in the form of a plurality of circular rings having a diameter gradually increasing based on a central axis which is opened for draw-in of the guide wire 10 from the outside. Accordingly, a plurality of electric wires connected to the roller driving body 225 may be disposed in the form of passing through the plurality of plated rings, respectively. Since the plated rings are entirely plated in a circumferential direction, even if the rotational electrode plate 235 is rotated, an electrical connection between each wire and a corresponding plated ring may be continuously maintained.

An electric wire guide frame 237 may be disposed at a rear of the rotational electrode plate 235. The electric wire guide frame 237 may serve to guide each of the electric wires so that each of the plurality of electric wires electrically connecting the external power source and the roller driving body 225 can enter a corresponding plated ring. For this purpose, the electric wire guide frame 237 may be formed with through-holes corresponding to the number of electric wires formed through the electric wire guide frame 237 in forward and rearward directions.

Upon initial setting for inserting the catheter 20 and the guide wire 10 into the target blood vessel, the guide wire 10 may have a front end thereof disposed at a branch point side of the branch portion 125 which forms the first connector 120 by the translational module 220. In addition, the guide wire 10 may be drawn into the catheter 20 by the translational module 220 and may be inserted nearby the target blood vessel through a continuous translational motion. In this case, the guide wire 10 may be rotated by the rotational module 230 when encountering a curved site of the blood vessel during the translational motion, and thus a direction of a front end of the guide wire may be switched to smoothly translate again.

In addition, when the catheter 20 is completely inserted into the target blood vessel, the guide wire 10 may be moved rearward by the translational module 220, and thus a front end of the guide wire may be returned to a position of initial setting.

The micro-catheter driving unit 300 may be provided at a rear of the catheter driving unit 100. When the guide wire 10 is drawn out from the inside of the catheter 20 and returned to the position of initial setting, the micro-catheter driving unit 300 may translate the micro-catheter 40 by drawing the micro-catheter 40 in a path coaxial with the catheter 20, which is different from draw-in and draw-out paths of the guide wire 10.

The micro-catheter driving unit 300 according to one embodiment of the present invention may be formed to include a front end mounting part 300A and a rear end mounting part 300B.

The front end mounting part 300A may be directly connected to a side of the catheter driving unit 100. A longitudinal front end portion of the micro-catheter 40 may be mounted on the front end mounting part 300A. The front end mounting part 300A may include a translational module 310 and a rotational module 320. In this case, the detailed configuration and operation of the translational module 310 and the rotational module 320 may be the same or similar to the detailed configuration and operation of the translational module 220 and the rotational module 230 provided in the guide wire driving unit 200, and thus a detailed description thereof will be omitted.

Upon initial setting for inserting the catheter 20 and the guide wire 10 into the target blood vessel, the front end mounting part 300A may be directly connected to the catheter driving unit 100, and thus the front end mounting part 300A may move together when the catheter driving unit 100 moves. In this case, upon initial setting for inserting the catheter 20 and the guide wire 10 into the target blood vessel, the longitudinal front end of the micro-catheter 40 may not be mounted on the front end mounting part 300A.

When the catheter 20 is completely inserted into the target blood vessel and the front end of the guide wire 10 is returned to the position of initial setting, the longitudinal front end of the micro-catheter 40 may be mounted on the front end mounting part 300A.

The rear end mounting part 300B may be spaced rearward of the front end mounting part 300A. Upon initial setting for inserting the catheter 20 and the guide wire 10 into the target blood vessel, when the front end mounting part 300A is moved by the movement of the catheter driving unit 100, the rear end mounting part 300A may not be affected by the movement, but maintain a fixed position. The rear end mounting part 300B may be connected to the micro-guide wire driving unit 400. The rear end of the micro-catheter 40 may be mounted on the rear end mounting part 300B. As shown in FIG. 11, the rear end mounting part 300B may include a third connector 330 for mounting the rear end of the micro-catheter 40. The third connector 330 may be formed to have the same structure as that of the first and second connectors 120 and 210. The third connector 330 may serve to provide a connection passage through which the micro-guide wire 30 positioned at the other longitudinal end can be inserted into the micro-catheter 40 mounted at one longitudinal end.

After the catheter 20 is completely inserted into the target blood vessel and the front end of the guide wire 10 is returned to the position of initial setting, the micro-catheter 40 may be first set to have a first tension upon setting for mounting the micro-catheter 40 on the micro-catheter driving unit 300 in order to insert the micro-catheter 40 and the micro-guide wire 30 into the target micro-blood vessel. In other words, as shown, the micro-catheter 40 may be connected in a loose state between the front end mounting part 300A and the rear end mounting part 300B.

In this state, in order to carry out a vascular intervention, the translational module 220 provided in the front end mounting part 300A may allow the front end of the micro-catheter 40, in which a longitudinal rear end thereof is fixed to the rear end mounting part 300B, to translate in the forward direction, and thus the micro-catheter 40 may be drawn into the catheter 20. Accordingly, during the vascular intervention, the micro-catheter 40 may have a second tension having strength increased more than the first tension. In other words, the micro-catheter 40 may be changed from a loose state to a tight state, as shown.

Here, the rear end mounting part 300B may include a micro-catheter translational driving body 340. The micro-catheter translational driving body 340 may provide power to move the rear end mounting part 300B, and thus the micro-catheter 40 may be translated. In this case, the micro-catheter translational driving body 340 may be synchronized with the catheter translational driving body 150 that provides power to move the catheter driving unit 100. Accordingly, during the vascular intervention, when the rear end mounting part 300B is moved by the micro-catheter translational driving body 340 in order to translate the micro-catheter 40, the catheter driving unit 100 and the front end mounting part 300A connected thereto may be moved at the same speed and distance as the rear end mounting part 300B by the catheter translational driving unit 150 synchronized with the micro-catheter translational driving body 340, thereby continuously maintaining the second tension of the micro-catheter 40 during the vascular intervention. In this case, when the catheter 20 and the micro-catheter 40 reach the end of the blood vessel which encounters the micro-blood vessel, through synchronization of the micro-catheter translational driving unit 340 and the catheter translational driving unit 150, the micro-catheter translational driving body 340 and the catheter translational driving body 150 may be released from the synchronization, and only the micro-catheter translational driving body 340 may be driven. Accordingly, only the micro-catheter 40 may continue to translate inside the micro-blood vessel.

The micro-guide wire driving unit 400 may be provided at the micro-catheter driving unit 300, more particularly, at the rear of the rear end mounting part 300B. The micro-guide wire driving unit 400 may draw the micro-guide wire 30 into the micro-catheter 40 and insert the micro-guide wire nearby the target micro-blood vessel by translating the micro-guide wire 30, and rotate the micro-guide wire 30 coaxially with the catheter 40. In this case, the front end of the micro-guide wire 30 mounted on the micro-guide wire driving unit 400 may be disposed at the other longitudinal end of the third connector 330 provided on the rear mounting part 300B.

The micro-guide wire driving unit 400 may include a translational module 410 and a rotational module 420. In this case, the detailed configuration and operation of the translational module 410 and the rotational module 420 may be the same as the detailed configuration and operation of the translational module 220 and the rotational module 230 provided in the guide wire driving unit 200, and thus a detailed description thereof will be omitted.

Upon initial setting for inserting the micro-catheter 40 and the micro-guide wire 30 into the target blood vessel, the micro-guide wire 30 may be mounted on the micro-guide wire driving unit 400. The translational module 410 may translate the micro-guide wire 30 mounted as above, and thus the micro-guide wire 30 may be drawn into the micro-catheter 40 and thus inserted nearby the target micro-vessel. The rotational module 420 may rotate the translating micro-guide wire 30 when the translating micro-guide wire 30 encounters a curved site of the micro-blood vessel, thereby controlling a front end direction of the micro-guide wire 30. As a result, the micro-guide wire 30 may continuously translate toward the target blood vessel.

A conveying unit 500 may receive a driving force from the catheter translational driving body 150 and the micro-catheter translational driving body 340, so as to convey the catheter driving unit 100 and the micro-catheter driving unit 300 along a longitudinal direction of the catheter 20.

The conveying unit 500 may include a base part 510, a first partition 520, a second partition 530, a support rod 540, a rack 550, and a pinion 560.

The base part 510 may be a frame that provides a base surface of the robot for vascular intervention 1000. The first partition 520 and the second partition 530 may be provided at both longitudinal ends of the base part 510. The support rod 540 may be provided between the first partition 520 and the second partition 530. The rack 550 may be provided on an upper surface of the base part 510 in a longitudinal direction of the robot for vascular intervention 1000. The pinion 560 may be gear-coupled with the rack 550, and may be operated by receiving a driving force from the catheter translational driving body 150 or the micro-catheter translational driving body 340. Accordingly, the catheter driving unit 100 and the micro-catheter driving unit 300, which are mounted on an assembly of the rack 550 and the pinion 560, may move in the longitudinal direction of the robot for vascular intervention 1000.

In this case, the pinion 560 may be connected to each of the catheter driving unit 100 and the micro-catheter driving unit 300 so that the catheter driving unit 100 and the micro-catheter driving unit 300 can individually move, and each of the catheter translational driving body 150 and the micro-catheter translational driving body 340 may provide a driving force to the pinion 560 connected to the catheter driving unit 100 and the micro-catheter driving unit 300, respectively. Meanwhile, the support rod 540 may provide a guide path for movement of the catheter driving unit 100 and the micro-catheter driving unit 300.

The catheter guide unit 600 may perform a function of supporting the catheter 20 while being folded in the longitudinal direction of the catheter 20. The catheter guide unit 600 may be provided in a tubular form extending in one direction. In this case, the catheter guide unit 600 may have a hollow therein in the longitudinal direction so that the catheter 20 can be inserted and moved, and both longitudinal ends of the catheter guide unit 600 may be opened. In one embodiment of the present invention, the catheter guide unit 600 may have a telescope structure for folding.

Hereinafter, a method for driving a robot for vascular intervention according to one embodiment of the present invention will be described with reference to FIGS. 12 to 19.

FIGS. 12 to 19 are views for explaining a method for driving a robot for vascular intervention according to one embodiment of the present invention.

Referring to FIG. 12, the method for driving the robot for vascular intervention according to one embodiment of the present invention may include an initial setting step (S110), a guide wire draw-in step (S120), a guide wire return step (S130), and a micro-catheter mounting step (S140), a micro-catheter draw-in step (S150), a micro-guide wire draw-in step (S160), and a translational movement step (S170).

First, as shown in FIG. 13, in the initial setting step (S110), the catheter 20 may be mounted inside the catheter guide unit 600. In this case, in the initial setting step (S110), a longitudinal rear end of the catheter 20 may be drawn into and held at one longitudinal end of the main body which forms a first connector 120. And in the initial setting step (S110), the guide wire 10 may be mounted on the guide wire driving unit 200, and then the translational module 220 may be driven so that a front end of the guide wire 10 can be disposed to reach a branch point side of the branch portion 125 which forms the first connector 120. In this case, in the initial setting step (S110), the micro-catheter 40 and the micro-guide wire 30 may not be mounted on the micro-catheter driving unit 300 and the micro-guide wire driving unit 400.

Then, as shown in FIG. 14, in the guide wire draw-in step (S120), the translational module 220 may be driven, so that the guide wire 10 disposed at the branch point side of the branch portion 125 can translate and thus the guide wire 10 can be drawn into the catheter 20. Subsequently, in the guide wire draw-in step (S120), the translational module 220 may be driven to continuously translate the guide wire 10, and thus the guide wire 10 may be inserted nearby the target blood vessel. In this case, in the guide wire draw-in step (S120), when the translating guide wire 10 encounters a curved site of the blood vessel, the rotational module 230 may be driven to rotate the translating guide wire 10, thereby controlling a front end direction of the guide wire 10. Accordingly, the guide wire 10 may be smoothly inserted nearby the target blood vessel.

Meanwhile, in the guide wire draw-in step (S120), after the guide wire 10 is inserted nearby the target blood vessel, the catheter translational driving body 150 may be driven to translate the catheter 20, and thus the catheter 20 can be inserted up to the target blood vessel. In this case, the catheter 20 may be translated by the movement of the catheter driving unit 100. In addition, when the catheter driving unit 100 is moved as above, the front end mounting part 300A of the micro-catheter driving unit 300 directly connected to the rear of the catheter driving unit 100 may be also moved together.

In the guide wire draw-in step (S120), like the guide wire 10, when the translating catheter 20 encounters a curved site of the blood vessel, the catheter rotational driving body 110 may be driven to rotate the translating catheter 20, thereby controlling a front end direction of the catheter 20. Accordingly, the catheter 20 may be smoothly inserted up to the target blood vessel.

Then, as shown in FIG. 15, in the guide wire return step (S130), in a state in which the catheter 20 is inserted up to the target blood vessel, the translational module 220 of the guide wire driving unit 200 may be driven to move the guide wire (10) rearward, so as to return the guide wire 10 to the position of initial setting. Accordingly, the longitudinal front end of the guide wire 10 may be positioned at the branch point side of the branch portion 125.

Then, as shown in FIG. 16, in the micro-catheter mounting step (S140), the micro-catheter 40 may be mounted on the micro-catheter driving unit 300. Specifically, in the micro-catheter mounting step (S140), the longitudinal front end of the micro-catheter 40 may be mounted on the front end mounting part 300A, and the longitudinal rear end may be mounted on the rear end mounting part 300B which is spaced rearward of the front end mounting part 300A. In this case, in the micro-catheter mounting step (S140), the micro-catheter 40 may be mounted so that the longitudinal front end of the micro-catheter 40 can be positioned at the other longitudinal end of the main body 123 which forms the first connector 120.

Here, in the micro-catheter mounting step (S140), the micro-catheter 40 may be mounted so as to have a first tension. In other words, in the micro-catheter mounting step (S140), the micro-catheter 40 may be loosely mounted as shown.

Meanwhile, in the micro-catheter mounting step (S140), after the micro-catheter 40 is mounted, the micro-guide wire 30 may be mounted on the micro-guide wire driving unit 400.

Then, as shown in FIG. 17, in the micro-catheter draw-in step (S150), the translational module 310 provided at the front end mounting part 300 may allow the front end of the micro-catheter 40, in which a longitudinal rear end thereof is fixed to the rear end mounting part 300B, to translate forward, and thus the micro-catheter 40 may be drawn into the catheter 20. Accordingly, the micro-catheter 40 may have a second tension having strength increased more than the first tension set upon setting. In other words, the micro-catheter 40 may be changed from a preset loose state to a tight state, as shown.

Then, as shown in FIG. 18, in the micro-guide wire draw-in step (S160), the translational module 410 provided at the micro-guide wire driving unit 400 may be driven to translate the micro-guide wire 30, and thus the micro-guide wire 30 may be drawn into the micro-catheter 40. Subsequently, in the micro-guide wire draw-in step (S160), the translational module 410 may be driven to translate the micro-guide wire 30, and thus the micro-guide wire 30 may be inserted nearby the target blood vessel. In this case, in the micro-guide wire draw-in step (S160), when the translating micro-guide wire 30 encounters a curved site of the blood vessel, the rotational module 420 provided at the micro-guide wire driving unit 400 may be driven to rotate the translating micro-guide wire 30, thereby controlling a front end direction of the micro-guide wire 30. Accordingly, the micro-guide wire 30 may be smoothly inserted nearby the target micro-blood vessel.

Finally, as shown in FIG. 19, in the translational movement step (S170), after the micro-guide wire 30 is inserted nearby the target micro-blood vessel, the micro-catheter translational driving body 340 may be driven to translate the micro-catheter 40, and thus the micro-catheter 40 may be inserted nearby the target micro-blood vessel. In this case, the micro-catheter 40 may be translated by the movement of the micro-catheter driving unit 300.

Here, since the micro-catheter translational driving body 340 may be synchronized with the catheter translational driving body 150 provided at the catheter driving unit 100, when the micro-catheter driving unit 300 is moved by the micro-catheter translational driving body 340, the catheter driving unit 100 and the front end mounting part 300A connected thereto may be also moved together. Accordingly, the micro-catheter 40 may maintain a second tension, that is, in a tight state.

Here, in the translational movement step (S170), the micro-catheter translational driving body 340 and the catheter translational driving body 150 may be synchronized together up to the end of the blood vessel which encounters the micro-blood vessel, so that the catheter 20 and the micro-catheter 40 may be translated together. However, the catheter 20 having a relatively large diameter may not be inserted into the micro-blood vessel. Thus, in the translational movement step (S170), when the catheter 20 and the micro-catheter 40 reach the end of the blood vessel which encounters the micro-blood vessel, the micro-catheter translational driving body 340 and the catheter translational driving body 150 may be released from the synchronization, and then only the micro-catheter translational driving body 340 may be driven. Accordingly, the catheter 20 may be stopped from translating at the end of the blood vessel which encounters the micro-blood vessel, and the micro-catheter 40 may continuously translate into the micro-blood vessel and thus may be inserted up to the target micro-blood vessel.

In this case, although not shown, the driving and release of the synchronized micro-catheter translational driving body 340 and the catheter translational driving body 150 may be controlled by a controller. The controller may be provided at a side of the master apparatus of the system for vascular intervention.

Although the invention has been described in detail with reference to exemplary embodiments, the scope of the present invention is not limited to a specific embodiment and should be interpreted by the attached claims. In addition, those skilled in the art should understand that many modifications and variations are possible without departing from the scope of the present invention.

What is claimed is:

1. A robot for vascular intervention, the robot comprising:
   a guide wire;
   a micro-catheter;
   a micro-guide wire;
   a catheter;
   a catheter driving unit for rotating and translating the catheter extending in a longitudinal direction while having the longitudinal direction as an axis;
   a guide wire driving unit provided at a side of the catheter driving unit, the guide wire driving unit being configured to draw the guide wire into the catheter by translating the guide wire, and the guide wire driving unit being configured to rotate the guide wire coaxially with the catheter;
   a micro-catheter driving unit provided at a rear of the catheter driving unit, the micro-catheter driving unit being configured to translate the micro-catheter in a path coaxial with the catheter that is different from draw-in and draw-out paths of the guide wire when the guide wire is drawn out from an inside of the catheter; and
   a micro-guide wire driving unit provided at a rear of the micro-catheter driving unit, and the micro-guide wire driving unit being configured to draw the micro-guide wire into the micro-catheter by translating the micro-guide wire, and the micro-guide wire driving unit being configured to rotate the micro-guide wire coaxially with the micro-catheter,
   wherein the micro-catheter driving unit comprises:
      a front end mounting part connected to the catheter driving unit and on which a longitudinal front end of the micro-catheter is mounted; and
      a rear end mounting part spaced rearward of the front end mounting part, connected to the micro-guide wire driving unit, and on which a longitudinal rear end of the micro-catheter is mounted,
   wherein the catheter driving unit comprises a catheter translational driving body and the rear end mounting part comprises a micro-catheter translational driving body,
   wherein the catheter is configured to translate as the catheter driving unit is moved by the catheter translational driving body, and the micro-catheter is configured to translate as the rear end mounting part is moved by the micro-catheter translational driving body,
   wherein, when the catheter and the micro-catheter are configured to be inserted toward a target blood vessel, the catheter translational driving body is configure to move the catheter driving unit at a speed equal to or faster than a speed at which the micro-catheter translational driving body moves the rear end mounting part, and
   wherein, when the catheter and the micro-catheter are configured to be drawn out from the target blood vessel, the catheter translational driving body is configured to move the catheter driving unit at a speed equal to or slower than a speed at which the micro-catheter translational driving body is configure to move the rear end mounting part.

2. The robot of claim 1, wherein the catheter driving unit and the front end mounting part are configured to be translated upon initial setting, but the longitudinal front end of the micro-catheter is not mounted on the front end mounting part.

3. The robot of claim 2, wherein, during the vascular intervention, the rear end mounting part and the micro-guide wire driving unit are configured to interwork with a translational motion of the catheter driving unit and the front end mounting part, in which both longitudinal ends of the micro-catheter are mounted on the front end mounting part and the rear end mounting part, respectively.

4. The robot of claim 3, wherein, upon setting for mounting the micro-catheter on the micro-catheter driving unit, the micro-catheter has a first tension.

5. The robot of claim 4, wherein, during the vascular intervention, the micro-catheter is configured to have a second tension having a strength increased more than the first tension upon the initial setting.

6. The robot of claim 1, wherein the catheter driving unit comprises a first connector providing a connection passage between the catheter and the guide wire, and the catheter and the micro-catheter.

7. The robot of claim 6, wherein the first connector comprises:
   a main body having a hollow formed therein, in which one longitudinal end is open to draw in and hold the catheter, and another longitudinal end is connected to the micro-catheter driving unit; and
   a branch portion branched from one longitudinal side of the main body, in which a hollow is formed therein to communicate with the hollow of the main body, and a longitudinal end is connected to the guide wire driving unit.

8. The robot of claim 7, wherein, upon initial setting, a longitudinal rear end of the catheter is configured to be drawn into and held at the one longitudinal side of the main body, and a front end of the guide wire is configured to be disposed at a branch point side of the branch portion.

9. The robot of claim 8, wherein, when the front end of the guide wire is configured to return to a position of the initial setting, a front end of the micro-catheter is configured to be disposed at the another longitudinal end of the main body.

10. The robot of claim 1, wherein each of the guide wire driving unit, the micro-catheter driving unit, and the micro-guide wire driving unit comprises:
   a translational module including a plurality of conveying rollers arranged along one direction, a guide roller disposed on a first conveying roller of the plurality of conveying rollers, the guide roller being configured to rotate relative to the first conveying roller, and a roller driving body configured to rotate the plurality of conveying rollers; and
   a rotational module connected to the translational module to rotate the translational module while having the longitudinal direction as the axis.

11. The robot of claim 10, wherein each of the guide wire, the micro-catheter, and the micro-guide wire is translated by the translational module, and is rotated by rotation of the translational module while having the longitudinal direction as the axis.

12. A robot for vascular intervention, the robot comprising:
   a guide wire;
   a micro-catheter;
   a micro-guide wire;
   a catheter;

a catheter driving unit for rotating and translating the catheter extending in a longitudinal direction while having the longitudinal direction as an axis;

a guide wire driving unit provided at a side of the catheter driving unit, the guide wire driving unit being configured to draw the guide wire into the catheter by translating the guide wire, and the guide wire driving unit being configured to rotate the guide wire coaxially with the catheter;

a micro-catheter driving unit provided at a rear of the catheter driving unit, the micro-catheter driving unit being configured to translate the micro-catheter in a path coaxial with the catheter that is different from draw-in and draw-out paths of the guide wire when the guide wire is drawn out from an inside of the catheter; and a micro-guide wire driving unit provided at a rear of the micro-catheter driving unit, and the micro-guide wire driving unit being configured to draw the micro-guide wire into the micro-catheter by translating the micro-guide wire, and the micro-guide wire driving unit being configured to rotate the micro-guide wire coaxially with the micro-catheter, wherein the micro-catheter driving unit comprises:
  a front end mounting part connected to the catheter driving unit and on which a longitudinal front end of the micro-catheter is mounted; and
  a rear end mounting part spaced rearward of the front end mounting part, connected to the micro-guide wire driving unit, and on which a longitudinal rear end of the micro-catheter is mounted, wherein the catheter driving unit comprises a catheter translational driving body and the rear end mounting part comprises a micro-catheter translational driving body, wherein the catheter is configured to translate as the catheter driving unit is moved by the catheter translational driving body, and the micro-catheter is configured to translate as the rear end mounting part is moved by the micro-catheter translational driving body, wherein, when the catheter and the micro-catheter are configured to be inserted toward a target blood vessel, the catheter translational driving body is configure to move the catheter driving unit at a speed equal to or faster than a speed at which the micro-catheter translational driving body moves the rear end mounting part, wherein, when the catheter and the micro-catheter are configured to be drawn out from the target blood vessel, the catheter translational driving body is configured to move the catheter driving unit at a speed equal to or slower than a speed at which the micro-catheter translational driving body is configure to move the rear end mounting part, and wherein each of the guide wire driving unit, the micro-catheter driving unit, and the micro-guide wire driving unit comprises:
  a translational module including a plurality of conveying rollers arranged along one direction, a guide roller disposed on a first conveying roller of the plurality of conveying rollers, the guide roller being configured to rotate relative to the first conveying roller, and a roller driving body configured to rotate the plurality of conveying rollers; and
  a rotational module connected to the translational module to rotate the translational module while having the longitudinal direction as the axis;

wherein the rotational module comprises:
  a rotational driving body;
  a gear coupled to a rotational shaft of the rotational driving body; and
  a rotational electrode plate which is rotated in engagement with the gear and includes a plurality of plated rings having a diameter gradually increasing based on an opened central axis, in which wires of the roller driving body are individually connected to each of the plurality of plated rings.

\* \* \* \* \*